United States Patent [19]

James et al.

[11] Patent Number: 4,822,527
[45] Date of Patent: Apr. 18, 1989

[54] PROCESS FOR PREPARATION OF ANTHRAQUINONES AND FLUORENONES

[75] Inventors: David E. James, Batavia; Neal R. Nowicki, St. Charles, both of Ill.

[73] Assignee: Amoco Corporation, Chicago, Ill.

[21] Appl. No.: 134,839

[22] Filed: Dec. 14, 1987

[51] Int. Cl.$^4$ .................... C07C 50/18; C07C 45/00
[52] U.S. Cl. ................................ 260/369; 260/687 R; 568/320
[58] Field of Search ................ 260/369, 689; 568/320

[56] References Cited

U.S. PATENT DOCUMENTS 4,185,023  1/1980  Handrick et al. ................... 260/369
4,490,297  12/1984  Feld et al. ........................... 562/493

Primary Examiner—Richard L. Raymond
Assistant Examiner—Raymond Covington
Attorney, Agent, or Firm—Gunar J. Blumberg; William H. Magidson; Ralph C. Medhurst

[57] ABSTRACT

A process is disclosed for producing cyclized aromatic compounds by the liquid-phase air oxidation of 2-methyl-substituted biphenyls and diphenylmethanes in an acetic acid medium in the presence of a cobalt-manganese-bromine catalyst or a zirconium-cobalt-manganese-bromine catalyst wherein the mole ratio of cobalt-to-manganese is about 1.0:0.1 to about 1.0:10.0 and the ratio of zirconium-to-cobalt is about 0.005:1.0 to about 0.20:1.0, and mole ratio of bromine to total metals of said cobalt-manganese-bromine catalyst or zirconium-cobalt-manganese-bromine catalyst is from about 0.2:1.0 to about 20.0:1.0, which process comprises conducting the reaction in a batch process at a temperature of from 75° C. to about 250° C. at a pressure of from 1 to 100 atmospheres, or continuously in two stages comprising a first-stage reaction at a temperature of about 75° C. to about 200° C. and a second-stage reaction at a temperature of about 150° C. to about 250° C. and recycling the cobalt-manganese catalyst or the zircnium-cobalt-manganese catalyst by oxalate precipitation of the catalyst at temperatures of about 110° C. to about 200° C. prior to the separation of mother liquor and using about 0.25 to about 2.5 moles of oxalic acid per mole of cobalt and manganese or mole of zirconium-cobalt-manganese and continuously recycling the recovered catalyst metals to the oxidation stages. The products of this novel process, anthraquinones and fluorenones, are useful for the manufacture of dyestuffs and pharmaceuticals.

5 Claims, No Drawings

4,822,527

PROCESS FOR PREPARATION OF ANTHRAQUINONES AND FLUORENONES

FIELD OF THE INVENTION

This invention relates to a process for the preparation of anthraquinones and fluorenones and their substituted derivatives.

BACKGROUND OF THE INVENTION

In general, the common methods of synthesis of ketones can be divided into (1) synthesis from acid halides and organometallic compounds, (2) synthesis from carboxylic acids, (3) Friedel-Crafts reactions, and (4) enolate condensations.

Synthesis from acid halides and organometallic compounds has been extensively used but costs of the organometallic reagents are relatively expensive and care must be used in handling. The use of carboxylic acids and their salts for ketone synthesis suffers from the disadvantage that the method will produce in general only the symmetrical ketones in good yields. The Friedel-Crafts acylation reactions generally give good yields. However, their use is restricted by the orientation of the acyl group introduced and the metal halides are expensive with attendant waste disposal problems. Enolate condensations give a variety of products; however, the overall yields are frequently not so good as those that can be obtained by other methods, and procedures frequently are more involved.

For example, as is well-known, the important methods of formation of benzophenone, i.e., benzophenone and its substituted derivatives, are the following: (1) oxidation of diphenylmethanes or benzohydrols, e.g., by chromic acid or by oxygen in presence of a catalyst, for example, as is taught in U.S. Pat. No. 2,859,274; (2) hydrolysis of ketone chlorides; (3) condensation of benzoyl halides with benzene, its homologues, and substituted derivatives having a reactive position, in presence of AlCl$_3$ or other catalyst, or under high pressure, as taught in U.S. Pat. No. 2,528,789; (4) reaction of a benzonitrile (or benzoyl halide) with a phenylmagnesium halide; (5) distillation of calcium or other suitable benzoate (Ann 12, 41).

Preparation of anthraquinone specifically has been proposed by several different processes: (1) the Diels-Alder reaction of butadiene on 1,4-naphthoquinone, (2) oxidation of anthracene in the presence of catalysts, (3) Friedel-Crafts reaction with benzene and phthalic anhydride, (4) oxidation of suitable precursors such as indane. In the Friedel-Crafts process, since a large amount of aluminum chloride is necessary, disposal of the wastes from the process is difficult. Furthermore, since isomerization reactions, rearrangement reactions, and elimination reactions occur in the process, many by-products derived from these reactions contaminate the product. Oxidation of anthracene is economically accomplished only when relatively pure anthracene is available at moderate costs. The Diels-Alder reaction suffers from the high cost of naphthoquinone. U.S. Pat. Nos. 3,699,134; 3,872,134; 3,872,135; 4,002,653; 4,036,860; 4,036,861; and 4,215,063 teach typical processes for manufacture of anthraquinone by oxidation of diphenylmethane compounds. These processes produce many by-products.

Preparation of fluorenones has been proposed by several different processes also: (1) the heating of salts of diphenyl-o-carboxylic acid or its salts produces fluorenone, (2) the diazonium compound of o-amino-benzophenone gives fluorenone with evolution of nitrogen, (3) the oxidation of phenanthraquinone. Fluorenone-carboxylic acids can be obtained by oxidation of fluoranthene with chromic acid, or by heating isodiphenic acid with concentrated sulfuric acid, or from 2'-aminobenzophenone-2-carboxylic acid by the action of nitrous acid. Fluorenone-1,7-dicarboxylic acid can be obtained by the action of permanganate on retene-quinone. Retene is defined as 1-methyl-7-isopropyl-phenanthrene. These processes produce many by-products.

As a result of these difficulties, considerable investigations have been carried out in efforts to develop syntheses of anthraquinones and fluorenones whereby the desired products in good yield are obtained by simple economic methods. This invention relates to a method for preparation of anthraquinones and fluorenones in good yield. The process can be by batch or by continuous method.

SUMMARY OF THE INVENTION

A process is disclosed for preparation of anthraquinones or fluorenones and their substituted derivatives by oxidation under mild conditions of the corresponding 2-methyl-substituted biphenyls and diphenylmethanes in the presence of an oxygen-containing gas and a cobalt-manganese-bromine catalyst at a temperature of from about 75° C. to about 250° C. at a pressure of from about 1 atmosphere to about 100 atmospheres.

DETAILS OF THE INVENTION

This novel invention is a method to prepare anthraquinone and fluorenone, and their substituted derivatives by contacting 2-methyl-substituted biphenyls and diphenylmethanes with a catalytic composition comprised of cobalt, manganese, and bromine compounds. More specifically, this invention is a method to prepare anthraquinone and fluorenone and their derivatives in good yield.

Our novel process relates to the liquid-phase air oxidation of 2-methyl-substituted diphenylmethane to anthraquinone in a mother liquor comprising an acetic acid medium wherein the weight ratio of 2-methyl-substituted diphenylmethane to acetic acid is in the range of from about 1:1 to about 1:20, preferably from about 1:4 to about 1:20, using cobalt, manganese, and/or other variable-valence metals, such as zirconium, plus bromine. Our novel invention is a process for the oxidation of 2-methyldiphenylmethane with molecular oxygen to anthraquinone under liquid-phase conditions in the presence of a cobalt-manganese-bromine catalyst at a temperature within the range of from about 75° C. to about 250° C. and a pressure from about 1 atmosphere to about 100 atmospheres. Other compounds which may be suitable for oxidation by this process are 2-methylbenzophenone and diphenylmethyl alcohols. The process can be by batch or continuous method.

In one aspect, our process can be a continuous process for producing anthraquinone by the liquid-phase air oxidation of 2-methyldiphenylmethane in a mother liquor comprising an acetic acid medium in the presence of a cobalt-manganese-bromine catalyst wherein the mole ratio of cobalt to manganese is from about 1.0:0.1 to about 1.0:10.0, and the mole ratio of bromine to total metals of the cobalt-manganese-bromine catalyst is from about 0.2:1.0 to about 20.0:1.0, preferably from about 3.0:1.0 to 10:1.0, bromine moles to total metal moles. The process can comprise conducting the reaction in two stages comprising a first-stage reaction at a temperature of about 75° C. to about 200° C. and a second-stage reaction at a temperature of about 150° C. to about 250° C., recovering the cobalt-manganese catalyst by oxalate precipitation of the catalyst using about 0.25 to about 2.5 moles of oxalic acid per total moles of cobalt and manganese and recycling the recovered cobalt and manganese compounds to the oxidation stages. Preferably, the mole ratio of the oxalic acid to the cobalt-manganese catalyst is about 0.5 to about 1.5.

In another aspect, the present invention can be a continuous process for producing anthraquinone by the liquid-phase air oxidation of 2-methyldiphenylmethane in a mother liquor comprising an acetic acid medium in the presence of a zirconium-cobalt-manganese-bromine catalyst wherein the mole ratio of zirconium-to-cobalt in the catalyst is from about 0.005:1.0 to about 0.20:1.0, preferably from about 0.01:1 to about 0.1:1.0, and the mole ratio of bromine to total metals of the zirconium-cobalt-manganese-bromine catalyst is from about 0.2:1.0 to about 20.0:1.0, preferably from about 3.0:1 to 10:1, bromine moles to total metal moles. The process can comprise conducting the reaction in two stages comprising a first-stage reaction at a temperature of about 75° C. to about 200° C. and a second-stage reaction at a temperature of about 150° C. to about 250° C., recovering the zirconium-cobalt-manganese catalyst by oxalate precipitation of the catalyst using about 0.25 to about 2.5 moles of oxalic acid per total moles of zirconium, cobalt, and manganese and continuously recycling the recovered zirconium-cobalt-manganese compounds to the oxidation stages. Preferably, the mole ratio of oxalic acid to zirconium-cobalt-manganese catalyst is about 0.5 to about 1.5.

In a continuous mode of operation, the catalyst is preferably recovered and recycled. Since the catalyst metals may coprecipitate with the anthraquinone product during crystallization, our novel process can include a catalyst recovery process which comprises a high temperature of about 110° C. to about 200° C. and an oxalate precipitation in a separate step. In our recovery process, high cobalt recoveries can be expected. Cobalt is the most expensive component of the catalyst.

In the recovery process, only small amounts of oxalic acid are required, usually about a 1:1 mole ratio with the catalyst metals; however, we can use mole ratios of oxalic acid to total cobalt and manganese of about 0.25:1 to 2.5:1. In our recovery process, the oxalate salts form rapidly, even from cobalt and manganese, or cobalt, manganese and zirconium, previously tied up as insoluble salts. The oxalates are readily recovered from the acetic acid solvent, in which they are insoluble, by high temperature separation, by, for example, high pressure centrifugation, or by hydroclones.

Temperatures in excess of about 200° C. cannot be used in our recovery process, since the oxalate salts of cobalt, manganese and zirconium decompose. The thermal instability of the oxalate salts enables us to recycle these compounds to the 2-methyldiphenylmethane oxidation reactors. Under our process oxidation conditions of about 150° C. to about 250° C., the oxalate salts regenerate to the active catalyst metals.

Our instant invented process also comprises a process for producing fluorenones from substituted biphenyls by the liquid-phase air oxidation of substituted biphenyls in a mother liquor comprising an acetic acid medium to a fluorenone product wherein weight ratio of substituted biphenyl to acetic acid is in the range of about 1:1 to about 1:20, preferably from about 1:4 to about 1:20, pressure is in the range of from about 1 atmosphere to about 100 atmospheres, in the presence of a cobalt-manganesebromine catalyst or a zirconium-cobalt-manganese-bromine catalyst wherein the mole ratio of zirconium-to-cobalt in the catalyst is from about 0.005:1.0 to about 0.2:1.0, preferably about 0.01:1 to about 0.10:1. Mole ratio of bromine to total metals of the cobalt-manganese-bromine or zirconium-cobalt-manganese-bromine catalyst is from about 0.2:1.0 to about 20.0:1.0, preferably from about 3.0:1.0 to about 10.0:1.0, bromine moles to total metal moles. The process can comprise conducting the oxidation in two stages, comprising a first-stage reaction at a temperature of about 75° C. to about 200° C. and a second-stage oxidation at a temperature of about 250° C. wherein both air and catalyst are added during the oxidation stages, recovering the cobalt-manganese metals or the zirconium-cobalt-manganese metals of said catalyst by oxalate precipitation of metals of said catalyst, using about 0.25 to about 2.5 moles of oxalic acid for the total moles of the cobalt-manganese metals or zirconium, cobalt and manganese metals of said catalysts and recycling the recovered cobalt-manganese compounds or zirconium-cobalt-manganese compounds to the oxidation stages. Preferably, mole ratio of said oxalic acid to said cobalt-manganese or zirconium-cobalt-manganese of said catalyst is about 0.5:1.0 to about 1.5:1.0.

In summary, the instant invention comprises a process for producing cyclized aromatic compounds comprising anthraquinones and fluorenones and carboxy derivatives of said aromatic compounds which process comprises liquid-phase air oxidation of a feedstock selected rrom the group consisting of 2-methyldiphenylmethane, 2-methylbiphenyl and derivatives of said 2-methyldiphenylmethane and said 2-methylbiphenyl to said anthraquinones and fluorenones in a mother liquid comprising an acetic acid medium wherein weight ratio of said feedstock to acetic acid is in the range of from about 1:1 to about 1:20, in the presence of a cobalt-manganese-bromine catalyst wherein the mole ratio of cobalt to manganese is about 1.0:0.1 to about 1.0:10.0, and mole ratio of bromine to total metals of said catalyst is from 0.2:1.0 to about 20.0:1.0, the process comprising oxidation of said feedstock at a temperature within the range of from about 75° C. to about 250° C. at a pressure of from about 1 to about 100 atmospheres, preferably said weight ratio of said feedstock to acetic acid is in the range of from about 1:4 to about 1:20, said mole ratio of cobalt-to-manganese is from about 1.0:0.1 to about 1.0:10.0, and said mole ratio of bromine to total metals of said catalyst is from about 3.0:1.0 to about 10.0:1.0.

The instant invention also comprises a process for producing cyclized aromatic compounds comprising anthraquinones and fluorenones and carboxy derivatives of said aromatic compounds which process comprises liquid-phase air oxidation of a feedstock selected from the group consisting of 2-methyldiphenylmethane, 2-methylbiphenyl and derivatives of said 2-methyldiphenylmethane and said 2-methyldiphenyl to said anthraquinones and fluorenones in a mother liquor comprising an acetic acid medium wherein weight ratio of said feedstock to acetic acid is in the range of from about 1:1 to about 1:20, in the presence of a zirconium-cobalt-manganese-bromine catalyst wherein the mole ratio of zirconium to cobalt is about 0.005:1.0 to about 0.20:1.0; the mole ratio of cobalt to manganese is from about 1.0:0.1 to about 1.0:10.0, and mole ratio of bromine to total metals of said catalyst is from about 0.2:1.0 to about 20.0:1.0, the process comprising oxidation of said feedstock at a temperature within the range of from about 75° C. to about 250° C. at a pressure from about 1 to about 100 atmospheres, preferably said weight ratio of said feedstock to acetic acid is in the range of from about 1:4 to about 1:20, said mole ratio of zirconium to cobalt in said catalyst is from about 0.01:1.0 to about 0.10:1.0 and said mole ratio of cobalt-to-manganese is from about 1.0:0.1 to about 1.0:10.0, and said mole ratio of bromine to total metals of said catalyst is from about 3.0:1.0 to about 10.0:1.0.

The instant invention also comprises a continuous process for producing cyclized aromatic compounds by the continuous liquid-phase air oxidation of a feedstock selected from the group consisting of 2-methyldiphenylmethane, 2-methylbiphenyl and derivatives thereof to anthraquinones and fluorenones in a mother liquor comprising an acetic acid medium wherein weight ratio of feedstock to acetic acid is in the range of from about 1:1 to about 1:20, in the presence of a cobalt-manganese-bromine catalyst wherein the mole ratio of cobalt-to-manganese is about 1.0:0.1 to about 1.0:5.0, mole ratio of bromine to total metals of the cobalt-manganese-bromine catalyst is from about 0.2:1.0 to about 20:1, bromine moles to total metals moles, the process comprising oxidation of said feedstock in two stages comprising a first-stage oxidation at a temperature of about 75° C. to about 200° C. and a second-stage oxidation at a temperature of about 150° C. to about 250° C. wherein both air and the cobalt-manganese-bromine catalyst are added to said oxidation stages and recovering the cobalt-manganese metals of said catalyst by oxalate precipitation of metals of said catalyst at temperatures of about 110° C. to about 200° C., using about 0.25 to about 2.5 moles of oxalic acid for the total moles of cobalt and manganese metals of said catalyst and continuously recycling the cobalt and manganese oxalates to said oxidation stages, preferably said weight ratio of said feedstock to acetic acid is in the range of from about 1:4 to about 1:20, said mole ratio of cobalt to manganese is from about 1.0:0.1 to about 1.0:10.0, and said mole ratio of bromine to total metals of said catalyst of from about 3.0:1.0 to about 10.0:1.0.

The instant invention comprises a continuous process for producing cyclized aromatic compounds acid by the continuous liquid-phase air oxidation of a feedstock selected from the group consisting of 2-methyldiphenylmethane, 2-methylbiphenyl and derivatives thereof to anthraquinones and fluorenones in a mother liquor comprising an acetic acid medium wherein weight ratio of feedstock to acetic acid is in the range of from about 1:1 to about 1:20 in the presence of a zirconium-cobalt-manganese-bromine catalyst wherein the mole ratio of zirconium-to-cobalt is about 0.005:1.0 to about 0.20:1.0, the mole ratio of cobalt-to-manganese is about 1.0:0.1 to about 1.0:5.0, and mole ratio of bromine to total metals of said catalyst is from about 0.2:1.0 to about 20.0:1.0, which process comprises conducting the oxidation in two stages comprising a first-stage reaction at a temperature of about 75° C. to about 200° C. and a second-stage oxidation at a temperature of about 150° C. to about 250° C. wherein both air and the zirconium-cobalt-manganese-bromine catalyst are added to said oxidation stages and recovering the zirconium-cobalt-manganese metals of said catalyst by oxalate precipitation of metals of said catalyst at temperatures of about 110° C. to about 200° C., using about 0.25 to about 2.5 moles of oxalic acid for the total moles of the zirconium, cobalt and manganese metals of said catalyst and continuously recycling the zirconium-cobalt-manganese oxalates to said oxidation stages, preferably said weight ratio of feedstock to acetic acid is in the range of from about 1:4 to about 1:20, said mole ratio of zirconium-to-cobalt in said catalyst is from about 0.01:1.0 to about 0.10:1.0, and said mole ratio of said cobalt-to-manganese is from about 1.0:0.1 to about 1.0:10.0, and said mole ratio of bromine to total metals of said catalyst is from about 3.0:1.0 to about 1.0:10.0.

The following examples illustrate the process of the instant invention but are not to be construed as limiting the scope of the invention.

EXAMPLE I

The following example illustrates the batch oxidation of 2-methyldiphenylmethane. 1.64 g 2-methyldiphenylmethane (0.009 moles), 100 ml acetic acid, 0.042 g cobalt acetate (0.00017 moles), 0.041 g manganese acetate (0.00017 moles), and 0.103 g sodium bromide (0.0010 moles) were added to a reactor. Reaction temperature was 194° F. (90° C.) at atmospheric pressure. The reaction was allowed to run for a full period of seven (7) days. Removal of the acetic acid solvent by evaporation resulted in precipitation of the product, 9-10-anthraquinone, which was determined by thin layer chromatographic analysis on silica gel using methylene chloride as eluent versus the known component.

EXAMPLE II

The batch procedure of Example I was repeated with 2.0 g of 2-methyldiphenylmethane (0.011 moles) with the same catalyst at the same temperature and atmospheric pressure. Reaction time was 7 days. Ratio of cobalt to 2-methyldiphenylmethane (2-MDM) was 0.015 moles Co to each mole of 2-MDM. Theoretical yield of 2-benzoylbenzoic acid was 2.49 g. Recovered solids were 1.30 g. Yield of anthraquinone was 7 mole%. Recycle of 2-benzoylbenzoic acid and subsequent cyclization in a continuous method can increase yield of anthraquinone to approximately a theoretical 52 (mole) % yield based upon the solids recovery of 1.30 g.

EXAMPLE III

The batch procedure of Example I was repeated with 2.0 g trimethylbiphenyl (0.010 mole) with the same catalyst at the same temperature and atmospheric pressure. Reaction time was four (4) days (96 hours). Ratio of cobalt to trimethylbiphenyl was 0.017 moles Co per mole of trimethylbiphenyl. Theoretical yield to tricarboxybiphenyl was 2.86 g. Details are in Table I.

TABLE I

| Preparation of 2,6-DCF Mole Ratios-Br:Catalyst Metals-3:1 | |
|---|---|
| Catalyst | |
| Co(OAc)$_2$ (0.0100 g Co; 0.00017 mole Co) | 0.042 g |
| Mn(OAc)$_2$ (0.0092 g Mn; 0.00017 mole Mn) | 0.041 g |
| NaBr (0.080 g Br; 0.0010 mole Br) | 0.103 g |
| Feed | |
| Trimethylbiphenyl (0.010 mole) | 2.0 g |
| Acetic Acid | 100 ml |
| Reaction Conditions | |
| Temperature | 90° C. |
| Pressure, Atm. | 1 |

TABLE I-continued

| Preparation of 2,6-DCF Mole Ratios-Br:Catalyst Metals-3:1 | |
|---|---|
| Time, Hours | 96 |
| Product Recovery-Filtration | Hot |
| Ratio-Moles Br to Total Moles Catalyst Metals | 3:1 |
| Yields (wt) % | |
| 2,6-Fluorenonedicarboxylic Acid (2,6-DCF) | 11.5 |
| 2,4',5-Biphenyltricarboxylic Acid (TCBi) | 70.1 |
| 2,6-Benzcoumarindicarboxylic Acid (BzC) | 18.4 |
| Total | 100.0% |
| Total Solids Recovered | 1.24 g |
| Percent Theoretical Yield | 43.4% |

EXAMPLE IV

The procedure of Example III was repeated with an increase of NaBr to 0.206 g (0.16 g Br; 0.0020 mole Br). All other conditions were the same as in Example III. The increase in bromine concentration increased the relative weight percent of 2,6-DCF in the total solids recovered. Details are in Table II.

TABLE II

| Preparation of 2,6-DCF Mole Ratio-Br:Catalyst Metals-6:1 | |
|---|---|
| Catalyst | |
| Co(OAc)$_2$ (0.0100 g Co; 0.00017 mole Co) | 0.042 g |
| Mn(OAc)$_2$ (0.0092 g Mn; 0.00017 mole Mn) | 0.041 g |
| NaBr (0.160 g Br; 0.0020 mole Br) | 0.206 g |
| Feed | |
| Trimethylbiphenyl (0.010 mole) | 2.0 g |
| Acetic Acid | 100 ml |
| Reaction Conditions | |
| Temperature | 90° C. |
| Pressure, Atm. | 1 |
| Time, Hours | 96 |
| Product Recovery-Filtration | Hot |
| Ratio-Moles Br to Total Moles Catalyst Metals | 6:1 |
| Yields (wt) % | |
| 2,6-DCF | 34.1 |
| TCBi | 51.1 |
| BzC | 14.8 |
| Total | 100.0 |
| Total Solids Recovered | 1.10 g |
| Percent Theoretical Yield | 38.5% |

EXAMPLE V

The procedure of Example III was repeated with an increase in the catalyst metals present. All other conditions were the same as in Example III. The increase in catalyst metals concentration reduced the relative weight percent of 2,6-DCF in the total solids recovered. Details are in Table III.

TABLE III

| Preparation of 2,6-DCF Mole Ratio-Br:Catalyst Metals-1:1 | |
|---|---|
| Catalyst | |
| Co(OAc)$_2$ (0.030 g Co; 0.00050 mole Co) | 0.125 g |
| Mn(OAc)$_2$ (0.028 g Mn; 0.00050 mole Mn) | 0.123 g |
| NaBr (0.080 g Br; 0.0010 mole Br) | 0.103 g |
| Feed | |
| Trimethylbiphenyl (0.010 mole) | 2.0 g |
| Acetic Acid | 100 ml |
| Reaction Conditions | |
| Temperature | 90° C. |
| Pressure, Atm. | 1 |
| Time, Hours | 96 |
| Product Recovery-Filtration | Hot |
| Ratio-Moles Br to Total Moles Catalyst Metals | 1:1 |
| Yields (wt) % | |
| 2,6-DCF | 7.2 |
| TCBi | 79.2 |
| BzC | 13.6 |
| Total | 100.0 |
| Total Solids Recovered | 1.35 g |
| Percent Theoretical Yield | 47.2% |

EXAMPLE VI

The procedure of Example III was repeated with a reduced amount of solvent acetic acid present. All other conditions were relatively the same as in Example III by increasing the amount of catalyst and trimethylbiphenyl present. The increase in total solids recovered was considered to result from ease of handling the resulting larger quantity of product. Details are in Table IV.

TABLE IV

| Preparation of 2,6-DCF Low Solvent-Br:Catalyst Mole Ratio-3:1 | |
|---|---|
| Catalyst | |
| Co(OAc)$_2$ (0.030 g Co; 0.00050 mole Co) | 0.125 g |
| Mn(OAc)$_2$ (0.028 g Mn; 0.00050 mole Mn) | 0.123 g |
| NaBr (0.240 g Br; 0.0030 mole Br) | 0.309 g |
| Feed | |
| Trimethylbiphenyl (0.03 mole) | 6.0 g |
| Acetic Acid | 44 ml |
| Reaction Conditions | |
| Temperature | 90° C. |
| Pressure, Atm. | 1 |
| Time, Hours | 96 |
| Product Recovery-Filtration | Hot |
| Ratio-Moles Br to Total Moles Catalyst Metals | 3:1 |
| Yields (wt) % | |
| 2,6-DCF | 14.9 |
| TCBi | 79.1 |
| BzC | 6.0 |
| Total | 100.0 |
| Total Solids Recovered | 5.59 g |
| Percent Theoretical Yield | 65.2% |

EXAMPLE VII

The procedure of Example III was repeated but temperature was increased to 435° F. (224° C.), reaction pressure to 500 psig (33.4 atm) and reaction time decreased to 30 minutes. The bromine to catalyst metals ratio was 11:1, manganese to cobalt mole ratio was 3:1. Cobalt to trimethylbiphenyl ratio was reduced to 0.0035 moles Co to 1 mole of trimethylbiphenyl. Details are in Table V.

TABLE V

| Preparation of 2,6-DCF High Mn:Co ratio-High Br:Catalyst Metals Ratio | |
|---|---|
| Catalyst | |
| Co(OAc)$_2$ (0.026 g Co; 0.00044 mole Co) | 0.11 g |
| Mn(OAc)$_2$ (0.074 g Mn; 0.00135 mole Mn) | 0.33 g |
| HBr (48%) (1.56 g Br: 0.0196 Mole Br) | 3.3 g |
| Feed | |
| Trimethylbiphenyl (0.127 mole) | 24.8 g |
| Acetic Acid | 800 ml |
| Reaction Conditions | |
| Temperature, °F. | 435 |

TABLE V-continued
Preparation of 2,6-DCF
High Mn:Co ratio-High Br:Catalyst Metals Ratio

| | |
|---|---|
| Pressure, psig | 500 |
| Time, min. | 30 |
| Product Recovery-Filtration | Hot |
| Ratio-Moles Br to Total Moles Catalyst Metals | 11:1 |
| Ratio-Co:Trimethylbiphenyl (Moles) | 0.0035 |
| Yields (wt) % | |
| 2,6-DCF | 28.5 |
| TCBi | 39.3 |
| BzC | 32.2 |
| Total | 100.0 |
| Total Solids Recovered | 9.0 g |
| Percent Theoretical Yield | 25.3% |

What is claimed is:

1. A process for producing cyclized aromatic compounds comprising anthraquinones and fluorenones and carboxy derivatives of said aromatic compounds which process comprises liuqid-phase air oxidation of a feedstock selected from the group consisting of 2-methyldiphenylmethane, 2-methylbiphenyl and derivatives of said 2-methyldiphenylmethane and said 2-methylbiphenyl to said anthraquinones and fluorenones in a mother liquor comprising an acetic acid medium wherein weight ratio of said feedstock to acetic acid is in the range of from about 1:1 to about 1:20, in the presence of a coblat-managanese-bromine catalyst wherein the mole ratio of cobalt to managanese is about 1.0:0.1 to about 1.0:10.0, and mole ratio of bromine to total metals of said catlayst is from 3.0:1.0 to about 10.0:1.0, the process comprising oxidation of said feedstock at a temperature within the range of from about 75° C. to about 250° C. at a pressure of from about 1 to about 100 atmospheres.

2. The process of claim 1 wherein said weight ratio of said feedstock to acetic acid is in the range of from aobut 1:4 to about 1:20.

3. A continuous process for producing cyclized aroamtic compounds by the continuous liquid-phase air oxidation of a feedstock selected from the group consisting of 2-methyldiphenylmethane, 2-methylibiphenyl and derivatives thereof to anthraquinones and fluorenones in a mother liquor comprising an acetic acid medium wherein weight ratio of feedstock to acetic acid is in the range of from about 1:1 to about 1:20, in the presence of a cobalt-mangance-bromine catalyst wherein the mole ratio of cobalt-to-managanse is about 1.0:0.1 to about 1.0:5.0, mole ratio of bromine to total metals of the cobalt-manganese bromine catalyst is from about 3.0:1.0 to about 10.0:1.0, bromine moles to total metals moles, the process comprising oxidation of said feedstock in two stages comprising a first-stage oxidation at a temperature of about 75° C. to about 200° C. and a second-stage oxidation at a temperature of about 150° C. to about 250° C. wherein both air and the cobalt-manganese-bromine catalyst are added to said oxidation stages and recovering the cobalt-manganese metals of said catalyst by oxalate precipitation of metals of said catalyst at temperature of about 110° C. to about 200° C., using about 0.25 to about 2.5 moles of oxalic acid for the total moles of cobalt and manganese metals of said catalyst and continuously recycling the cobalt and manganese oxalates to said oxidation stages.

4. The process of claim 3 wherein said weight ratio of said feedstock to acetic acid is in the range of from about 1:4 to about 1:20.

5. In an improved process for producing cyclized aromatic compound comprising anthraquinons and fluorenones and carboxy derivatives of said aroamtic compounds wherein a feedstock selected from the group consisting of 2-methylidiphenylmethane, 2-methylbiphenyl, and derivatives of said 2-methyldiphenylmethane and said 2-methylbiphenyl is oxidized in the liquid phase in a mother liquor comprising an acetic acid medium in the presence of a cobalt-manganese-bromine catalyst to said anthraquinones and fluorenones, the improvement which comprises employing a catalyst providing a bromine-to-total metals mole ratio that is within the range of about 3.0:1.0 to about 10.0:1.0.

* * * * *

UNITED STATES PATENT OFFICE
CERTIFICATE OF CORRECTION

Patent No. 4,822,527  Dated 4/18/89

Inventor(s) James Nichols & Michelle Bonnett

It is certified that error appears in the above-identified patent and that said Letters Patent is hereby corrected as shown below:

On the title page, in the ABSTRACT, "zircnium-" should be --zirconium--
Col. 1, line 47, "DielsAlder" should be --Diels-Alder--
Col. 4, line 6, "manganesebromine" should be --manganese-bromine--
Col. 4, line 36, "rrom" should be --from--
Col. 9, line 38, "aobut" should be --about--
Col. 9, line 40, "aroamtic" should be --aromatic--
Col. 10, line 1, "methylibiphenyl" should be --methylbiphenyl--
Col. 10, line 6, "mangance" should be --manganese--
Col. 10, line 7, "managanse" should be --manganese--
Col. 10, line 9, "cobalt-manganese bromine" should be --cobalt-manganese-bromine
Col. 10, line 19, "temperature" should be --temperatures--
Col. 9, line 30, "managanese" should be --manganese--
Col. 10, line 29, "compound" should be --compounds--
Col. 10, line 29, "anthraquinons" should be --anthraquinones--
Col. 10, line 30, "aroamtic" should be --aromatic--
Col. 10, line 32, "2-methylidiphenylmethane" should be
                  --methyldiphenylmethane--

Signed and Sealed this

Ninth Day of January, 1990

Attest:

JEFFREY M. SAMUELS

Attesting Officer      Acting Commissioner of Patents and Trademarks

UNITED STATES PATENT OFFICE
CERTIFICATE OF CORRECTION

Patent No. 4,822,527        Dated April 18, 1989

Inventor(s) David E. James and Neal R. Nowicki

It is certified that error appears in the above-identified patent and that said Letters Patent is hereby corrected as shown below:

The inventors' names are incorrect on the Certificate of Correction dated January 9, 1990: They should read, "David E. James & Neal R. Nowicki."

Signed and Sealed this

Twenty-seventh Day of November, 1990

Attest:

HARRY F. MANBECK, JR.

*Attesting Officer*         *Commissioner of Patents and Trademarks*